(12) United States Patent
Madsen et al.

(10) Patent No.: US 8,849,368 B2
(45) Date of Patent: Sep. 30, 2014

(54) IMPLANTABLE ELECTRONIC DEVICES FOR DETECTING HYPOGLYCAEMIA USING EEG SIGNALS

(75) Inventors: Rasmus Madsen, Copenhagen (DK); Henning Beck-Nielsen, Odense (DK)

(73) Assignee: Hypo-Safe A/S, Lyngby (DK)

( * ) Notice: Subject to any disclaimer, the term of this patent is extended or adjusted under 35 U.S.C. 154(b) by 674 days.

(21) Appl. No.: 12/812,682

(22) PCT Filed: Jan. 2, 2009

(86) PCT No.: PCT/EP2009/050008
§ 371 (c)(1),
(2), (4) Date: Aug. 31, 2010

(87) PCT Pub. No.: WO2009/090110
PCT Pub. Date: Jul. 23, 2009

(65) Prior Publication Data
US 2010/0317955 A1   Dec. 16, 2010

(30) Foreign Application Priority Data

Jan. 14, 2008 (GB) .................................. 0800615.7

(51) Int. Cl.
| | | |
|---|---|---|
| *A61B 5/04* | (2006.01) | |
| *A61B 17/34* | (2006.01) | |
| *A61B 5/0478* | (2006.01) | |
| *A61N 1/00* | (2006.01) | |
| *A61M 25/06* | (2006.01) | |

(52) U.S. Cl.
CPC ........... *A61B 5/0478* (2013.01); *A61B 17/3468* (2013.01); *A61M 25/0668* (2013.01); *A61B 17/3439* (2013.01)
USPC ............ 600/377; 600/372; 600/544; 607/115

(58) Field of Classification Search
CPC .. A61B 5/0006; A61B 5/0476; A61B 5/0478; A61B 5/0482; A61B 17/3468; A61M 25/0668; A01B 12/006
USPC ................. 600/373, 377–378, 393, 544–545; 607/115–116
See application file for complete search history.

(56) References Cited

U.S. PATENT DOCUMENTS

| | | | |
|---|---|---|---|
| 6,572,542 B1 | 6/2003 | Houben et al. | |
| 6,754,472 B1 | 6/2004 | Williams et al. | |

(Continued)

FOREIGN PATENT DOCUMENTS

| | | |
|---|---|---|
| AU | 2007201370 A1 | 4/2007 |
| DE | 102004011217 A1 | 10/2005 |

(Continued)

OTHER PUBLICATIONS

International Search Report PCT/EP2009/050008 Jun. 19, 2009.
Todd C. Handy, "Event-related potentials: a methods handbook", 2004—XP009114048 pp. 167-188.
Kristal L. Johnson et al, "Brain Stem Response to Speech: A Biological Marker of Auditory Processing", Ear and Hearing, Oct. 2005, pp. 424-427.

(Continued)

*Primary Examiner* — Linda Dvorak
*Assistant Examiner* — Brian M Antiskay
(74) *Attorney, Agent, or Firm* — Sughrue Mion, PLLC (57) ABSTRACT

Apparatus for capturing EEG signals comprising an implantable signal capture unit (34) connected to a proximal end of at least one implantable electrode (32) is implanted by passing a tubular guide sheath (24,26) along a subcutaneous path from an implantation site, passing the distal end of a said electrode through said guide sheath to bring said signal capture unit to said implantation site, and withdrawing said guide sheath from the electrode while progressively axially splitting the guide sheath to enable its removal. The signal capture unit may have a housing having at least two electrode contacts on its for capturing EEG signals in operative connection with circuitry within said housing for receiving said EEG signals and for wireless transmission thereof for reception at a location exterior to the body of the patient.

2 Claims, 5 Drawing Sheets

(56) References Cited

U.S. PATENT DOCUMENTS

| | | |
|---|---|---|
| 2004/0044293 A1 | 3/2004 | Burton |
| 2004/0267152 A1* | 12/2004 | Pineda .................... 600/544 |
| 2006/0122676 A1 | 6/2006 | Ko et al. |
| 2006/0200038 A1* | 9/2006 | Savit et al. ................ 600/544 |
| 2007/0203548 A1 | 8/2007 | Pawelzik et al. |
| 2008/0183097 A1* | 7/2008 | Leyde et al. .............. 600/545 |

FOREIGN PATENT DOCUMENTS

| | | |
|---|---|---|
| WO | 98/36711 A1 | 8/1998 |
| WO | 2004/032788 A2 | 4/2004 |
| WO | 2005/094669 A1 | 10/2005 |
| WO | 2006/066577 A1 | 6/2006 |
| WO | 2007/144307 A2 | 12/2007 |
| WO | 2007/150003 A2 | 12/2007 |

OTHER PUBLICATIONS

A. James Rowan et al, Primer of EEG with a Mini-Atlas, Chapter 1, Butterworth Heinemann.

Mingui Sun et al, "Data Communication Between Brain Implants and Computer", IEEE Transactions on Neural Systems and Rehabilitation Engineering, Jun. 2003, vol. 11, No. 2, pp. 189-192.

Zhide Tang et al, "Circuit Model of Battery Recharging by Volume Conduction", Bioengineering Conference 2006, Proceedings of the IEEE 32nd Annual Northeast 2006, pp. 125-126.

Benjamin Blankertz et al, "The non-invasive Berlin Brain-Computer Interface: Fast Acquisition of Effective Performance in Untrained Subjects", Neuroimage, . 37, No. 2, Aug. 2007, Epub Mar. 1, 2007, pp. 539-550.

Current Practice of Clinical Electroencephalography, $3^{rd}$ Ed., Ebersole and Pedley, Editors, Chapter 4, pp. 72-74, Lippincott Williams & Wilkins, pub.

\* cited by examiner

IMPLANTABLE ELECTRONIC DEVICES FOR DETECTING HYPOGLYCAEMIA USING EEG SIGNALS

BACKGROUND OF THE INVENTION

The present application relates to implantable electronic devices, with particular but not exclusive relevance to implantable devices for detecting the onset of hypoglycaemia.

WO2006/066577 described implantable electronic devices for use in warning of impending hypoglycaemia. The described device had an implantable component positioned in the chest, or behind the neck, or elsewhere communicating with subcutaneously implanted electrodes in the scalp. An optional external part was described for signal processing, receiving data by wireless transmission from the implanted component.

PCT/EP2007/055628 provides an algorithm for use in processing signals for such hypoglycaemia detection.

The present application presents a number of practical improvements in connection with units of this general type.

BRIEF SUMMARY OF THE INVENTION

Accordingly, the present invention provides in a first aspect a method for implanting apparatus for capturing EEG signals comprising an implantable signal capture unit having connected thereto a proximal end of at least one implantable electrode having a free distal end, said method comprising passing a tubular guide sheath along a subcutaneous path from an implantation site, passing the distal end of a said electrode through said guide sheath to bring said signal capture unit attached to the proximal end of said electrode into said implantation site, and withdrawing said guide sheath from the electrode whilst progressively axially splitting the guide sheath to enable its removal.

Preferably, the proximal end of said electrode is sealed into the signal capture unit.

Preferably, the tubular guide sheath comprises at least one axial line of weakening enabling it to be pulled apart as it is withdrawn.

Preferably, a bundle of at least two electrodes is passed through said guide sheath.

Optionally, at least one further tubular guide sheath is passed from the implantation site along a second subcutaneous path and the distal end of at least a second said electrode is passed through said further tubular guide sheath as the signal capture unit is brought to the implantation site, and said further guide sheath is withdrawn from said second electrode whilst being progressively axially split to enable its removal from the electrode.

Preferably, said second electrode is a member of a bundle of at least two electrodes that are passed through said further tubular guide sheath.

Each electrode may have an elongate insulated body and an uninsulated portion at its tip or intermediate its length for gathering EEG signals.

Preferably, the length of the or each said electrode is no more than 6 cm.

Preferably, the implantation site is behind the ear of a human patient.

After the implantation, preferably a first electrode extends from the implantation site to gather EEG signals at a first location which is preferably within a circular zone of about 5 cm (more preferably approximately 2 cm, most preferably approximately 1 cm) diameter centred just above and behind the ear, preferably approximately on a line joining standard electrode location points C3 and T5, preferably at the centre of said line.

Preferably, a second electrode extends from the implantation site to gather EEG signals at a location which is preferably within a circular zone of about 5 cm diameter (more preferably approximately 2 cm, most preferably approximately 1 cm) centred approximately 1.5 cm vertically below the middle point of a line joining standard electrode locations C3 and T5. Preferably, the second location is approximately 1.5 cm below said first location.

Preferably the first and second electrodes form part of a common electrode bundle.

References to positions on the head at which to sense EEG signals herein are with reference to standard International 10-20 position mapping for EEG electrodes as described for instance in 'Primer of EEG with a Mini-Atlas', Rowan and Tolunsky (Butterworth Heinemann) Chapter 1, FIGS. 1-1 to 1-6, or the extended 10-20 system as described in 'Current Practice of Clinical Electroencephalography' third edition, Ebersole and Pedley Ed, Lippincott, Williams & Wilkiks pub, Chapter 4, pages 72-74.

Thus, preferably, two said electrodes are separated by at least 1.5 cm.

Preferably, the implanted apparatus cooperates in use with an EEG signal analysis unit for determining when EEG signals received from the said electrode indicate a specific physiological condition.

In accordance with this aspect of the invention, there is further provided a subcutaneously implantable EEG apparatus comprising at least one elongate, flexible electrode having a proximal end in permanent electrical connection with a signal capture unit contained in a housing, and a guide sheath extending over the electrode and running the length of the electrode, the guide sheath having an internal bore containing the electrode that is too small to pass over said housing, wherein said guide sheath has an axial line of weakness to allow manual splitting of the guide sheath and stripping of the guide sheath progressively from the electrode. All the optional or preferred features described herein in connection with implantation method may be used in connection with such a device.

In an alternative aspect, the invention provides an implantable apparatus for capturing and transmitting EEG signals comprising a housing suitable for subcutaneous implantation beneath the scalp of a patient and having at least two electrode contacts on the exterior thereof for capturing EEG signals in use, said electrodes being in operative connection with circuitry within said housing for receiving said EEG signals and for wireless transmission thereof for reception at a location exterior to the body of the patient.

Preferably, two said electrodes are separated by at least 1.5 cm.

Preferably, the longest external dimension of said apparatus is from 1.5 to 3 cm and also (but independently) the smallest external dimension of said apparatus does not exceed 0.5 cm.

In a still further aspect of the invention there is provided apparatus for use in preventing hypoglycaemia comprising an EEG based detector for the onset of hypoglycaemia operatively connected to an actuatable release device such as a pump for the administration to a patient of a hypoglycaemia preventing substance. For instance, upon triggering of an alarm state in response to impending hypoglycaemia, a preloaded capsule may be fractured to release said substance.

Preferably, the EEG based detector comprises an implantable signal capture unit operatively connected to at least two EEG sensor electrodes adapted for subcutaneous implantation.

Preferably, said pump is operatively connected to a reservoir containing glucose, glucagon.

The apparatus may further comprise a generator of an alarm signal such as a sound or vibration of mild electrical shock perceivable by a user of said apparatus.

The apparatus may be configured to initiate administration of said substance by said pump following a predetermined time lapse from the generation of a said alarm signal, and may comprise an input for a cancellation signal by said user such that input of said cancellation signal by the user prevents or halts actuation of said pump.

Preferred features of such devices that may be employed in EEG apparatus generally and in EEG apparatus for sensing the onset of hypoglycaemia in general also include the following. All of the preferred and optional features of the invention described herein may be used independently of each other and separately from the implantation method disclosed as the first independent aspect of the invention herein and from the other independently claimed aspects of the invention.

The implanted signal capture unit may be small enough (size of a hearing aid or smaller, e.g. 1-2 cm in diameter or other largest dimension, and not exceeding 0.5 cm thick) to be mounted in the human body at some appropriate place on the head, such as just behind the ear.

The device may comprise one or more electrodes that are placed subcutaneously, and define places where the EEG is physically measured, measurement electronics/hardware that the electrode is connected to, that amplifies and/or converts the EEG to digital form, a power source that supply the electronics with energy for operation, a housing part that encapsulates the measurement electronics in a biocompatible way, while allowing the electrode(s) to pass through and be connected to the measurement electronics.

The electrode(s) may be Magnetic Resonance Imaging (MRI) safe, e.g. comprising an electrode core that is MRI safe, given the characteristics of the material used. The material could in particular be a (90/10) mixture of Platinum and Iridium (Pt/IR) that is also biocompatible.

Preferably, the tip of the or each electrode is un-insulated. The main elongate body of the electrode being insulated, suitably by a coating of insulator which may be an electrode coating that is made of one or more of polyethylene and/or PTFE and/or silicone and/or other biocompatible insulating materials.

Where MRI safety is not required, the electrode(s) core may be made of the steel, making manufacturing costs lower.

A bundle of electrodes may comprise two or more electrodes of substantially the same physical length, which are each insulated over most of their length but have a sensing region which is uninsulated, different electrodes in the bundle having their sensing regions at different lengths from the signal capture unit. Normally, the sensing region of one electrode in the bundle will be at its distal end.

Each electrode in said bundle may be a single conductor filament or a may comprise multiple conductor filaments, typically wound together. Furthermore, each electrode in said bundle may be duplicated in case of breakage. Duplicated electrodes may be connected together, for instance at one or both of their proximal and distal ends.

The signal capture unit may be powered in various ways. It may be powered by a battery, which may be rechargeable.

Where the device power source is rechargeable it may be recharged by use of induction. Alternatively, the device may be powered continuously by induction from an external device such that there is no need for battery inside the human body. An external transmitting power source is in use placed close to the device to transfer power to the device by induction, allowing the device battery to be recharged. An alternative recharging method is described in Tang et al; Bioengineering Conference, 2006. Proceedings of the IEEE 32nd Annual Northeast 2006, pp 125-126.

Alternatively or additionally, the device may be powered and/or recharged by the energy that can be extracted from heat differentials or changes in the body, as in U.S. Pat. No. 6,131,581.

Alternatively or additionally, the device may be powered and/or recharged by another device that is mounted on the body. This other device may use the techniques described in U.S. Pat. No. 6,754,472 to transmit power to other devices.

Alternatively or additionally, the device may be powered and/or recharged by the kinetic energy that is generated from body movement as in WO2004/032788.

The function of the signal capture unit is to capture voltages sensed by the or each electrode for further processing to extract therefrom clinically significant information. The processing of the signals may be performed within the same housing as contains the signal capture unit or in a separately housed unit, so that the functional device is split up into two physical devices. The measured signals are transmitted from the one part of the device that is implanted, to another part of the device that is either located outside the body or internally at a location where a larger volume can be accommodated. The signals could in particular be transmitted to an outer device located on the human body, using the volume conduction techniques described in Sun et al; IEEE Transactions on Neural Systems and Rehabilitation Engineering, Vol. 11, No. 2, June 2003 pp 189-192 or in U.S. Pat. No. 6,754,472 Other transmission possibilities include Bluetooth, Sigbee, Wibree, RFID, Active RFID, and other wireless transmission methods.

The full functionality of the system may be split between four devices consisting of the implantable device for capturing the EEG signals, an external device for use in transmitting power and signals to the internal device and receiving signals therefrom, a pocket computer device in communication, e.g. wireless communication with the external device for processing or further processing the EEG signals, for providing information relating to the signals to the user or a clinician, including where desired alarm signals and status information.

Preferably, the device gives an estimate of whether a hypoglycaemic attack is impending, based on the signals that are measured.

Optionally, the device sends a signal to activate a nutrient (e.g. glucose or glucagon) pump that can increase the blood glucose level.

Alternatively the device sends a signal to activate such a pump, if the user does not react to the alarm in a predefined manner that shows that he is able to take actions to increase his glucose level by himself. This may involve the inputting of a code having a level of complexity, e.g. involving the inputting of at least three control signals.

Alternatively or additionally, the device gives an estimate of whether an epileptic attack is impending.

Alternatively the device monitors the time and quantity of epilepsy attacks, and stores this information for the physicians or other that might find the information useful.

Alternatively or additionally, the device gives an estimate of whether the person is intoxicated by alcohol or other drugs.

An alternative is also to give an alarm in case of lack of oxygen—can be very useful for newborns under observation or patients in intensive care units (NB in this case one may chose not to implant the device but only the electrode(s))

Alternatively or additionally, the device gives an estimate of the mental status of the person wearing it. This may include estimates of one or more or all of awareness, happiness, stress, tiredness, and consciousness. This could function either as a qualifier of the actual mental state or as an evaluation of the state over a period of time (did I sleep well last night? Was I stressed at my work today?)

The device may give an estimate of the brain stem response to the current auditory scene. Use may be made of the principles disclosed in Krista L. Johnson et al, Ear & Hearing October 2005, pp 424-427.

Features may be extracted from the brain stem response and/or from the general EEG signals. These features may be used to control the parameters in a hearing aid, for optimal hearing.

The purpose of the device may also be to monitor whether the person wearing the device is awake or alert (for instance as a modification of the driver alertness monitor of US2004/0044293) or to control an external device in particular for disabled persons but also for non-disabled persons e.g. as described in Blankertz et al, Neuroimage. 2007 Aug. 15; 37(2):539-50. Epub 2007 Mar. 1.

For instance, the purpose may be to control a wheelchair, a cell-phone, a computer, a mouse, a keyboard, a car, a PDA, a remote controlling device, and/or other wearable computational devices.

Alternatively or additionally, the purpose may be to control the functionality of a hearing aid, a cochlear implant, or other devices for hearing disabled persons. As such, the device may be a modification of a device for calibrating and adjusting a cochlear implant as described in WO98/36711. The functionality that should be controlled includes but is not limited to: volume, suppression of background noise, listening direction.

Alternatively or additionally, the purpose may be to monitor sleep rhythms and disorders.

Alternatively or additionally, the purpose may be to locate the physical origin of brain disorders.

BRIEF DESCRIPTION OF THE DRAWINGS

The invention will be further described an illustrated with reference to the accompanying drawings in which.

DETAILED DESCRIPTION OF THE INVENTION

Figure 1:
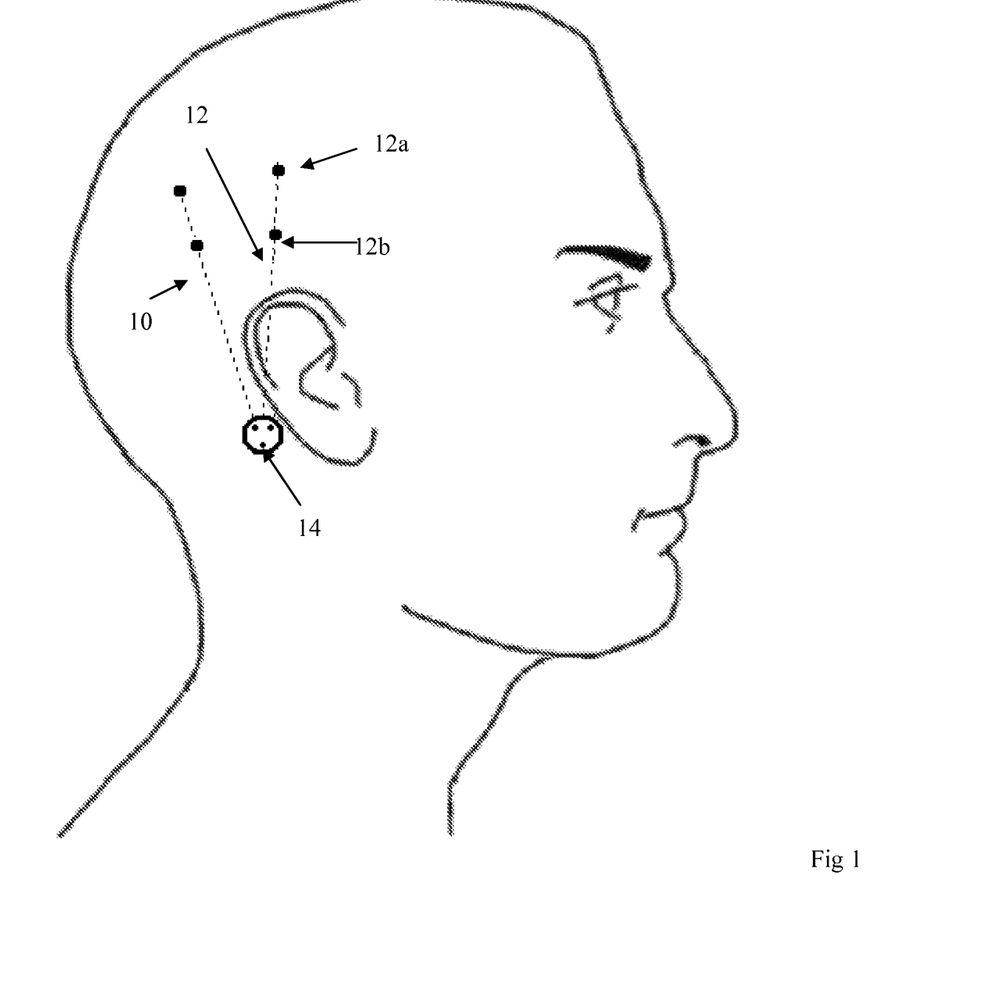
FIG. 1 shows two alternative preferred electrode and signal capture unit placement locations for use in an implanted EEG apparatus.

As seen in FIG. 1, components of apparatus used in the invention include an EEG electrode bundle 10 or alternatively or additionally 12 and EEG signal capture unit 14.

The illustrated alternative electrode bundles 10 or 12 each comprise a first electrode and a second electrode (12b in bundle 12), each being in the form of a metal wire with an insulating coating and each extending from the signal capture unit in which their respective proximal ends are sealed to a common distal end location the positions of which are as shown (12a in bundle 12). Both the first and the second electrodes in the bundle contain multiple (e.g. duplicate) single or multiple filament conductor wires, where each wire is uninsulated at a sensor (or signal gathering) location (12a and 12b in bundle 12), the sensor locations differing between the two electrodes, but each electrode preferably being of the same length to assist in implantation. One of the electrodes has a non-insulated end region defining its sensor location and the other has a non-insulated region approximately ¾ of the way from the proximal end towards the distal end thereof defining its respective sensor location. Two examples of preferred locations for the upper of the two electrode sensor locations and for the lower of the two electrode sensor locations in the bundle are shown.

Figure 2A:
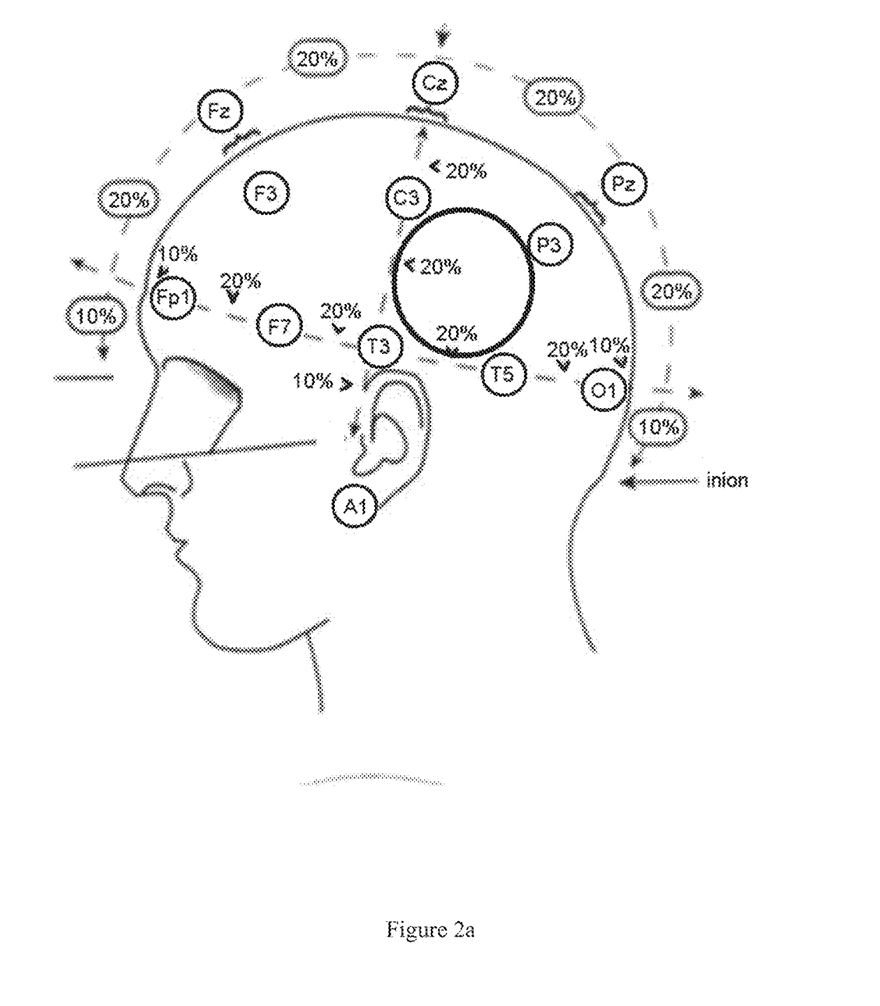
FIG. 2a shows a preferred electrode location zone marked on a standard electrode placement map.
Figure 2B:
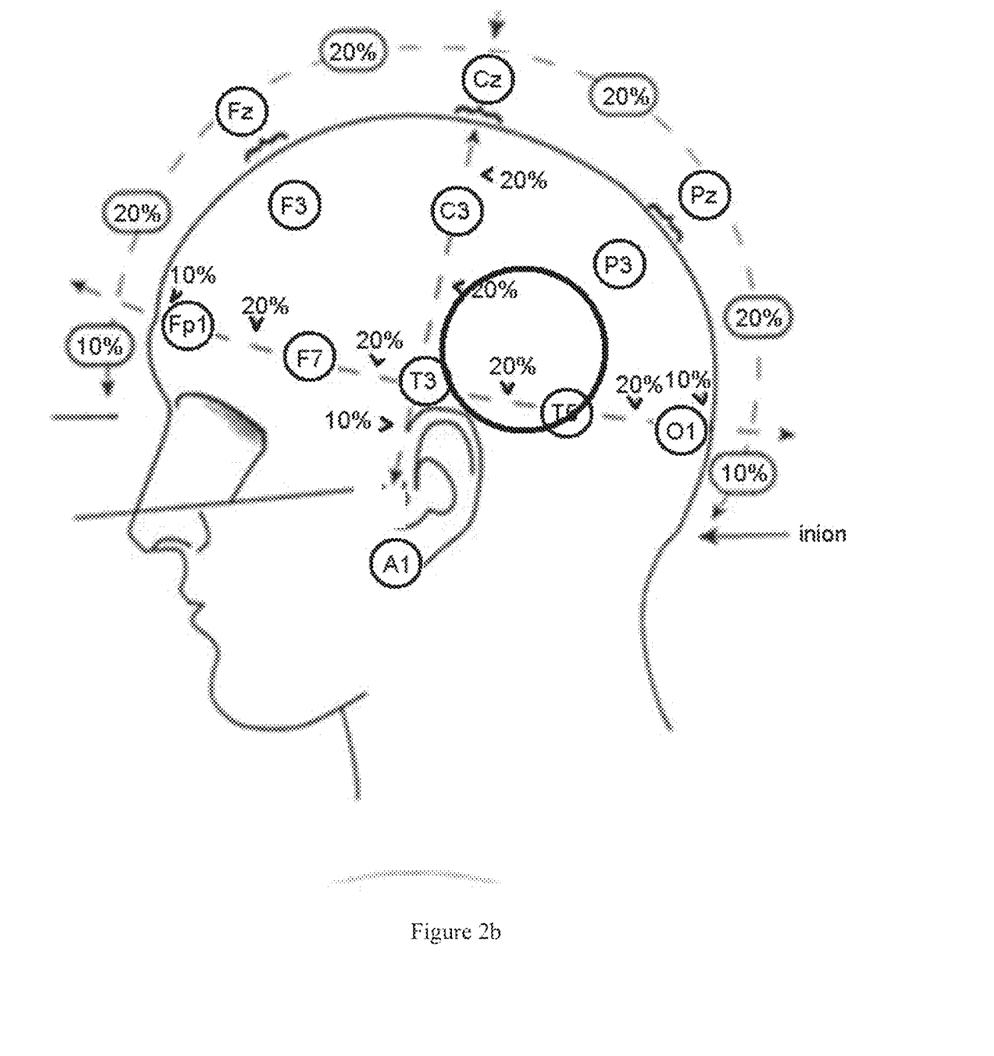
FIG. 2b shows a second preferred electrode location zone marked on the standard electrode placement map.

In FIG. 2a, a standard electrode location map on a head is shown with a preferred electrode location zone for the upper of the two electrode sensor locations, encompassing location 12a in FIG. 1. Here the electrode bundle extends to an electrode position within a circle around the mid point of the line joining standard electrode positions C3 and T5 and is preferably located at the centre of said circle or close thereto. The electrode bundle passes through a second electrode sensing position shown in FIG. 2b within a circle around a location 1.5 cm below the mid point of said C3-T5 line and is preferably located at the centre of said circle or close thereto. This encompasses the exemplified position 12b of FIG. 1.

Although two alternative electrode bundles are shown and either may be used, the one directed to the more forward illustrated position d preferred. Of course, both may be used together if desired and there may be more than two electrodes with respective sensing locations provided in the bundle or bundles used.

The electrodes within the bundle or bundles connected to the signal capture unit may optionally be up to 6.5 cm long, e.g. from 5.5 to 6.5 cm long, e.g. 6 cm long, providing between them 1 reference point and 1 or more channel contact points (sensor or signal gathering locations). The contact points may be made of stainless steel or a mixture of platinum iridium [Pt/Ir 90/10].

Each electrode preferably has two separate wires (whether single or multifilament) with separate contact points for each individual electrode. The separate wires of each electrode are connected together where the electrode is connected to the implanted signal gathering unit. This will reduce problems that could occur if an electrode wire should break or lose contact to the human body or the implantable device.

Each electrode therefore may consist of one or more wires. Each wire is un-insulated at a specific point, where it gathers the electrical signal. If a single wire is used as an electrode and breaks, the electrode will become noisy because of the bad connection. If more wires are un-insulated at the same place they will gather the same electrical signal. If these wires are short circuited inside the device, they can be used as one single signal source. Should one of two wires break, the signal will remain intact without noise.

The electrodes run subcutaneously, i.e. beneath the surface of the skin but outside the skull. The signal capture unit is implanted beneath the skin behind the ear of a human subject.

Figure 3:
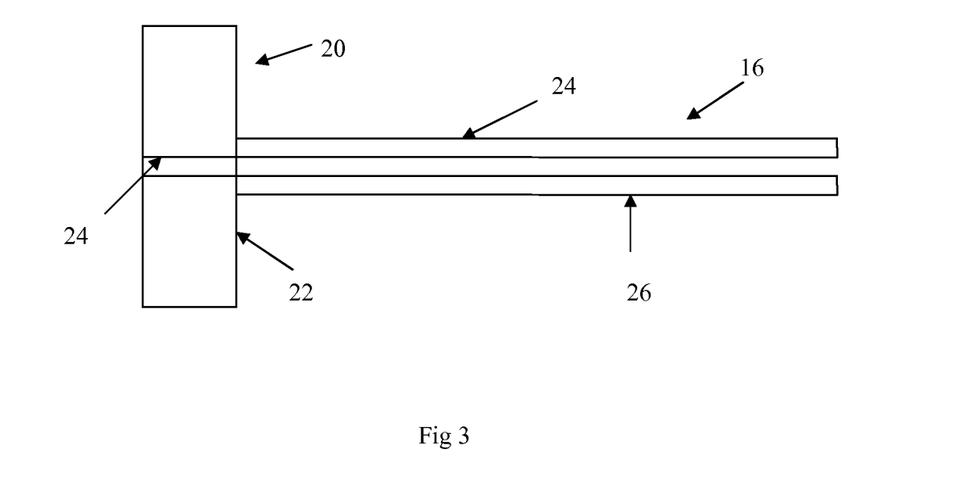
FIG. 3 shows in plan view a tubular guide sheath for use in implanting electrodes subcutaneously whilst attached to a signal capture unit.

Shown in FIG. 3 is a tubular guide sheath 16 of the same length as the electrodes, or a little longer, having a proximal end mounted in a plastics mounting block 20. The mounting block 20 has a through hole continuing the line of the bore of the guide sheath. The guide sheath is of plastics and is constructed as two half tubes 24,26 frangibly adhered to one another along axially running seams to form one cylindrical tube.

The mounting block is in two halves 20,22 which are frangibly adhered to one another by adhesive 24 and securely fixed each to a respective one of the two half tubes. Upon the application of some manual force, the two halves of the mounting block are easily separated and as they are pulled apart, the two half tubes are also separated progressively from their proximal ends.

The implantation of the EEG device shown in FIG. 3 is accomplished as follows. First, a pointed guide needle or stylet is inserted from the proximal end of the guide sheath through the mounting block and along the guide sheath bore to extend beyond its distal end. An incision is made of a sufficient size to provide an implantation site to contain the signal capture unit. The stylet is used to pass the guide sheath subcutaneously from the incision site to the desired distal EEG signal gathering point. Optionally, the action is repeated with a second guide sheath to position its end at a second distal EEG signal gathering site.

The stylet is withdrawn from the guide sheath and an electrode bundle 12 is passed therethrough to bring the signal capture unit 14 to the implantation site. The mounting block of the guide sheath is now split apart and the guide sheath is progressively pulled out while being progressively axially split until it is completely removed. The incision site is then closed.

Thus, it is avoided that the proximal ends of the electrodes have to be attached to the signal capture unit after the electrode bundle has been implanted. This makes the actual implantation process quicker and simpler and avoids the possibility of error in connecting the electrodes and enables them to be sealed against the ingress of body fluids and tested before implantation.

The analysis of captured EEG signals and the generation of feedback, such as an alarm, can be as described in WO2006/066577 and in PCT/EP2007/055628.

The signal capture unit is formed as a sealed unit containing the necessary electronics and power source within a housing of or coated with a biocompatible material such as PTFE, latex, polyethylene, silicone, or other biocompatible polymer. However, at least one part of the cover may be of or may expose a metal conductor providing a differential amplifier ground, allowing common mode signals to be rejected from an analog amplification circuit in the device.

An analog front end of the circuitry may have an impedance matched to that of the human body, which is about 10 kOhm at 10 Hz and may be provided with protective circuitry providing protection from electrostatic charges. A differential input amplifier used for first amplifying the EEG signals from the electrodes may have a high common mode rejection ratio (CMRR), optionally by using a right leg driver (RLD). A spectral range of 0.5-32 Hz is preferably captured from the EEG signals by the amplifiers and by analog to digital (A/D) converters. The noise level in the signals measured when they have been converted to digital form for white Gaussian noise is preferably such as to have a standard deviation below 2 μV, when compared with the raw EEG signal. The amplification is suitably such as to ensure that one least significant bit (LSB) is 1 μV. The amplification demand of the amplifiers is preferably such as to ensure that the EEG signal (+/−128 μV) plus DC drift is amplified to the dynamic range of the A/D converter. The amplified signal is preferably filtered to reject mains frequency hum, usually at 50 or 60 Hz. It is also desirable to damp frequencies above 32 Hz with 20 dB. Filtering of the EEG signal can be carried out digitally by oversampling the analog signal and filtering it after sampling, before downsampling to 64 Hz.

The implanted device may have options of either analyzing the EEG signals from the electrodes or storing and transmitting the EEG signals. When in the mode of analyzing, the device only transmits status information and alarm indications.

The logic in the algorithm may be allowed to make the analysis and data collection operations sleep for some time, when it is determined that analysis is unnecessary this lowers the power consumption, allowing the device to operate for a longer time on the same battery charge. Coefficients used for the analysis algorithm may be adjustable by user or clinician input allowing re-fitting the algorithm that analyses the EEG.

The implantable device is preferably be able to store some history/log information that may then be downloadable by an external device. During transmission of raw EEG data, data loss is 1 second of data per minute is acceptable.

Communication through the derma barrier may use an inductive coil that is also used for powering the device.

The inductive coils [inside and outside] may be aligned by a magnet ensuring good alignment and therefore high efficiency.

Use of a active RFID chip for the communication is preferable.

Radio communication between devices must normally use the MICS band for medical applications. The MICS band is constrained to the frequency range [402 MHz-405 MHz] and is be permitted in both the United States and the European Union. When the same frequency bands are not permissible in all geographical regions in which such devices may be used, a way of changing the transmission frequency and protocol may be included. Applicable radio technologies include (Zigbee, Z-wave, Elantech, Wibree (Nokia), Zarlink ZL70101 Active RFID tags). Radio transmission may preferably have a transmission range of at least 2 meters.

It is preferred that the chip technology used is a low power [1 volt] technology, especially if the implantable device is powered by battery, since the battery capacity is more stable for low voltage batteries. The implantable device could be powered by various power solutions, but inductive powering and battery powering are preferable.

The parameters in the implantable device may be fitted using one time programming [OTP].

Depending on the selected concept, either the external or implantable device may have a way of warning and communicating to the user. The information may be given by a sound or by a shaker function as known in cell phones.

Figure 4:
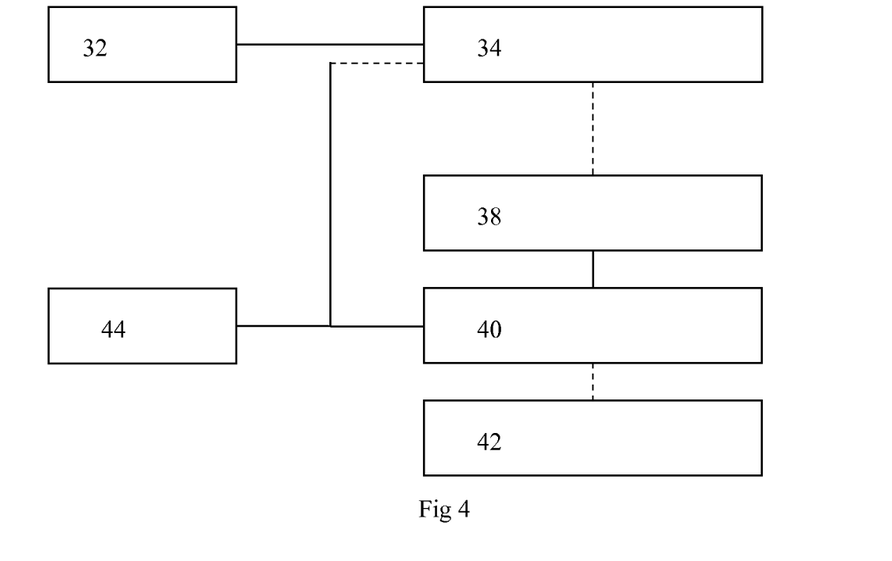
FIG. 4 is a schematic block diagram of a form of apparatus including a connected nutrient pump.

As illustrated in FIG. 4, one option within the scope of the invention involves EEG sensing electrodes 32 being connected to a signal capture unit 34 containing circuitry for transmitting data captured from the electrodes wirelessly (signified by the dotted connection) to a computation device 38 such as a palmtop computer. The EEG signals are digitized either in the signal capture unit 34 or in the palmtop 38 and are analysed in the palmtop 38 for the presence of patterns indicative of the onset of hypoglycaemia. Upon detection of such a condition, an alarm signal is triggered by the palmtop 38 and emitted from there and/or from the implanted signal capture unit 34 in response to a trigger signal from the palmtop 38 thereto.

The initiation of the alarm condition is communicated to a delay timer 40, which may be embodied in the palmtop 38, and starts a count down there. If within a preset time, the patient responds to the alarm by making a suitable input to an alarm cancellation unit 44, a signal is given from there to the countdown timer 40 to stop the countdown and is further communicated to the alarm to cancel the alarm. If however, the countdown timer reaches zero, an actuating signal is conveyed to a medicament/nutrient pump 42 which is implanted in the patient or worn by the patient and which administers a blood sugar boosting substance such as glucose or glucagon to prevent the patient slipping into a hypoglycaemic comatose state. The input required to the alarm cancellation unit 44 may be made sufficiently complex as to ensure that the patient is at a sufficiently high level of consciousness as to be able to deal adequately with their low blood sugar level themselves. It may for instance require the input of a code or a different input on each occasion in the form of the answer to a mathematical sum requiring computation.

The device is preferably be able to detect some critical failures that could occur during operation, and be able to log important statistical information that can be used by the users, doctors, and engineers to determine the history of operation. The following list is covering only parts of the situations that may be handled in case of device failure. In the case that the electrode wire breaks or gets a bad connectivity to the tissue, the device is preferably able to detect that failure. During such a failure, the device would either get a zero signal or a continuous noise signal. The algorithm in the device should preferably therefore be able to detect that the EEG signal is abnormal and communicate a warning to the user. In the case the software in the implantable device (and other devices) hangs, there may usefully be a functionality that resets the device so that it can start operating normally again. A watchdog timer that triggers a system reset if the main program, due to some fault condition, stops sending it regularly timed signals may be used, and if it runs down, the device is reset. The information about the event should preferably be logged and communicated to the user.

In the case where the process in the implantable device is trying to write to the system log that is full, the user should be made aware of this, so he can take the necessary precautions and empty the log. In this case the system should overwrite the oldest log entries. In the case where the system cannot write to the log file for some reason (e.g. not enough power) or there is a failed write error, the user should be alerted, so that the necessary precautions can be taken. If the power level in the implantable device is to low the user should be alerted so he can take the necessary precautions, e.g. align the external device with the implanted device.

If data packages are not received by the external device, the user should be informed so that he can take the necessary precautions, e.g. align the external device with the implant. If the EEG data that has been analyzed has been too noisy to analyze for a long time, the user should be informed about this. If the External device fails to get in contact with the implanted device, the user should be alerted. If there are CRC errors in data packages received from the implanted device, the user should be alerted so that the necessary precautions can be taken.

Figure 5:
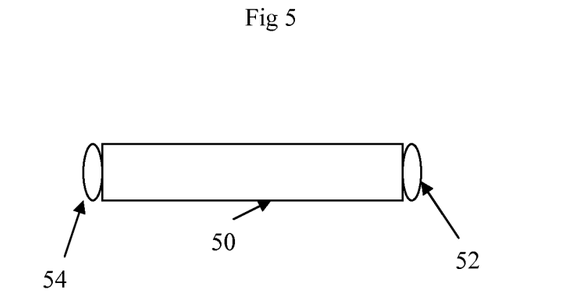
FIG. 5 shows an EEG signal capture unit incorporating electrodes in accordance with a separate aspect of the invention.

FIG. 5 shows a signal capture unit incorporating electrodes in accordance with a further independent aspect of the invention. As shown in FIG. 5, a fluid tight housing 50 suitable for subcutaneous implantation has within it circuitry which at least has the functions of receiving EEG signals from each of two electrodes 52,54 disposed at spaced locations on the exterior of the housing, and after optional processing of the signals transmitting them for reception in a separate external or implanted device. The signal capture unit may preferably contain circuitry for digitising said EEG signals received from the electrodes. The use of a signal capture unit in this form removes the need to run electrodes under the skin from signal gathering locations to a signal capture unit at a remote location, but, surprisingly, a sufficient EEG signal can be obtained using such a device to enable processing to identify the incipient onset of hypoglycaemia. The electrodes 52 and 54 are preferably from 1.5 to 3 cm or more preferably 1.75 to 2.5 cm apart and the largest dimension of the apparatus is preferably therefore no more than 2.5 cm. Preferably it is no more than 0.5 cm or more preferably 0.3 cm thick, such that it can be implanted beneath the scalp at the more forward position seen for electrode placement in FIG. 1. Of course, more than one unit as illustrated may be employed.

The user and the device may need to be able to communicate with each other during operation, e.g. the user may need to be able to communicate that an emitted hypoglycemia alarm has been received and the necessary precautions are being taken. The list below describes some methods that may be used alone or in combination for communication between the device and user.

- A pressure sensor mounted on the implanted device may measure if the user is applying a small force on the skin, at the location of the implanted device. Different pressure sequences could be used to communicate different messages, like e.g. Morse codes
- Different kinds of buttons on either the external device or pocket device could be used to communicate with the implanted device, using the wireless communication link to pass the information to the device.
- A vibrating transducer could be mounted on the internal or external device, enabling the device to communicate information to the user. The transducer could emit waves in the hearing frequency-range or vibrations that the user can feel, similar to the shaker function in a mobile phone. The waves that are emitted can use different frequencies and different modulated waveforms to communicate different messages to the user.

When impending hypoglycemia is detected by such a device it may be communicated to the user by giving the alarm sequence, such as one consisting of three short beep sequences, followed by three long beep sequences. The alarm sequence may be sent at frequent periodic intervals such as every 15 seconds until the user responds to the alarm. If the user acknowledges the alarm and takes the necessary precautions, he can respond by giving a deactivation code. If the alarm is given to the user via the pocket device, the user's cognitive state could be tested by e.g. asking him to perform an arithmetic test, and enter the result on the device. If the user is not capable of this, other people capable of interfering could be alarmed about the situation—or a glucagon pump is activated.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference in their entirety. No acknowledgement of any prior published document herein should be taken to be an admission or representation that the teaching thereof was common general knowledge in Australia or elsewhere at the date hereof.

The invention claimed is:

1. Apparatus for use in preventing hypoglycaemia comprising an EEG signal based detector which detects the onset of hypoglycaemia on the basis of EEG signals, operatively connected to a generator for generating an alarm signal perceivable by a user of said apparatus upon the detection of the onset of hypoglycaemia, and further operatively connected to a pump for the administration of glucose or glucagon to a patient upon detection of the onset of hypoglycaemia, said pump being operatively connected to a reservoir containing glucose or glucagon for administration, said operative connection between the detector and the pump comprising a processor configured to initiate administration of said glucose or glucagon by said pump following a predetermined time lapse from the generation of a said alarm signal by said alarm signal generator, and comprising an input for a wireless cancellation signal by said user such that input of said wireless cancellation signal by the user prevents or halts actuation of said pump by said processor.

2. Apparatus as claimed in claim 1, wherein the EEG based detector comprises an implantable signal capture unit operatively connected to at least two EEG sensor electrodes adapted for subcutaneous implantation.

\* \* \* \* \*